(12) United States Patent
Fuss et al.

(10) Patent No.: US 6,562,072 B1
(45) Date of Patent: May 13, 2003

(54) IMPLANT FOR INSERTION BETWEEN SPINAL COLUMN VERTEBRAE

(75) Inventors: Franz Konstantin Fuss, Wiener Neustadt (AT); Ronald J. Sabitzer, Vienna (AT)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 09/620,031

(22) Filed: Jul. 20, 2000

Related U.S. Application Data

(63) Continuation of application No. PCT/AT99/00015, filed on Jan. 22, 1999.

(30) Foreign Application Priority Data

Jan. 23, 1998 (AT) ................................................ 110/98

(51) Int. Cl.⁷ .................................................. A61F 2/44
(52) U.S. Cl. ................................. 623/17.11; 623/17.16
(58) Field of Search ......................... 623/17.11, 17.16, 623/20.28, 23.5, 23.76

(56) References Cited

U.S. PATENT DOCUMENTS

| | | | |
|---|---|---|---|
| 4,834,757 A | | 5/1989 | Brantigan |
| 4,904,261 A | * | 2/1990 | Dove et al. ................... 623/17 |
| 4,917,704 A | * | 4/1990 | Frey et al. .................... 623/17 |
| 5,071,437 A | | 12/1991 | Steffee |
| 5,171,281 A | | 12/1992 | Parsons et al. |
| 5,192,327 A | | 3/1993 | Brantigan |
| 5,861,041 A | * | 1/1999 | Tienboon .................... 623/17 |
| 6,111,164 A | * | 8/2000 | Rainey et al. ................. 623/16 |
| 6,409,765 B1 | * | 6/2002 | Bianchi et al. ............ 623/17.11 |
| 2002/0022886 A1 | * | 2/2002 | Fuss et al. ............... 623/17.11 |

FOREIGN PATENT DOCUMENTS

| | | |
|---|---|---|
| DE | 36 37 314 | 5/1988 |
| DE | 94 13 778 | 1/1996 |
| DE | 297 20 022 | 1/1998 |
| EP | 0369 603 | 5/1990 |
| EP | 0 599 419 | 6/1994 |
| FR | 2 736 537 | 1/1997 |
| WO | WO 90/00037 | 1/1990 |
| WO | WO 94/05235 | 3/1994 |
| WO | WO 95/10248 | 4/1995 |
| WO | WO 96/40014 | 12/1996 |
| WO | WO 97/23175 | 7/1997 |

\* cited by examiner

Primary Examiner—Paul B. Prebilic
(74) Attorney, Agent, or Firm—Barry R. Lipsitz; Douglas M. McAllister

(57) ABSTRACT

An implant for insertion between vertebrae of the verterbral column having a substantially rectangular or trapezoidal cross-section and covering faces adapted to face the adjacent vertebrae which are porous and/or designed with a profile. The implant has such a width that it substantially covers at the maximum the rear half of the vertebrae facing the spinous process, preferably at the maximum the rear third of the vertebrae facing the spinous process, and such a length that it substantially covers the rear region of the vertebrae. The limiting surface of the implant facing the inside of the vertebrae and extending in the direction of the adjacent vertebrae is convex. This enables an adequate and reliable supporting function to be achieved with only one implant and can easily be inserted sideways from behind.

22 Claims, 4 Drawing Sheets

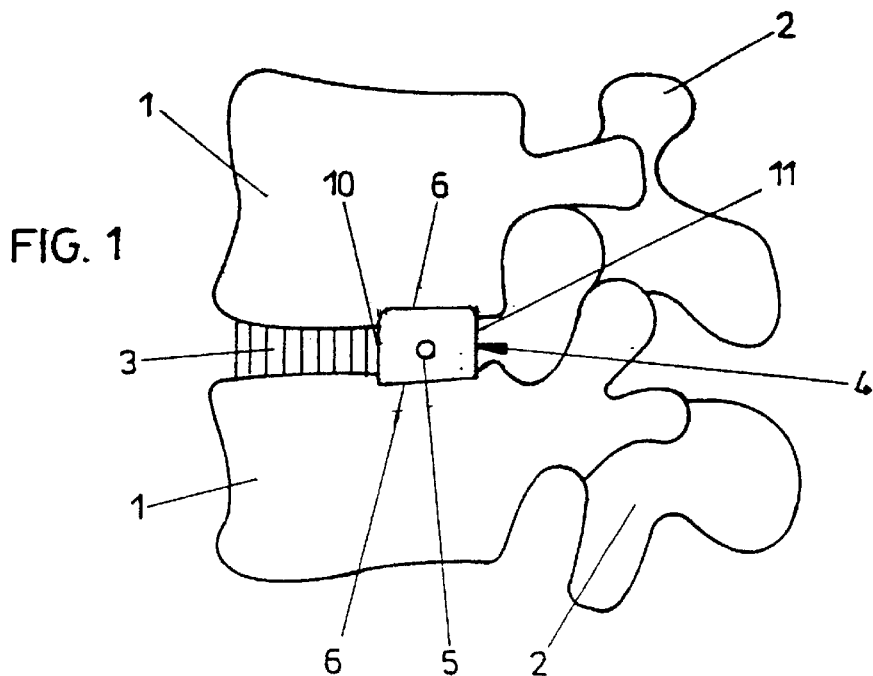
FIG. 1
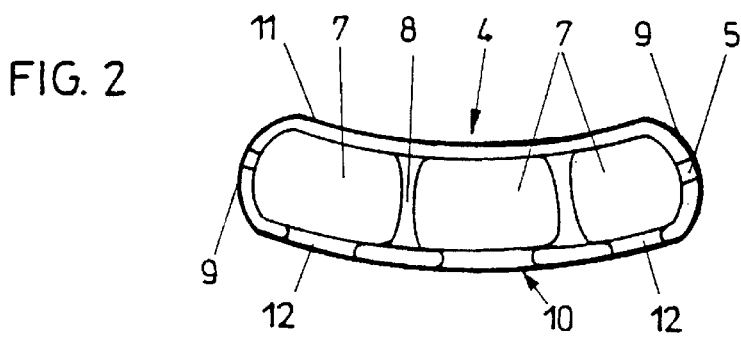
FIG. 2
FIG. 2a
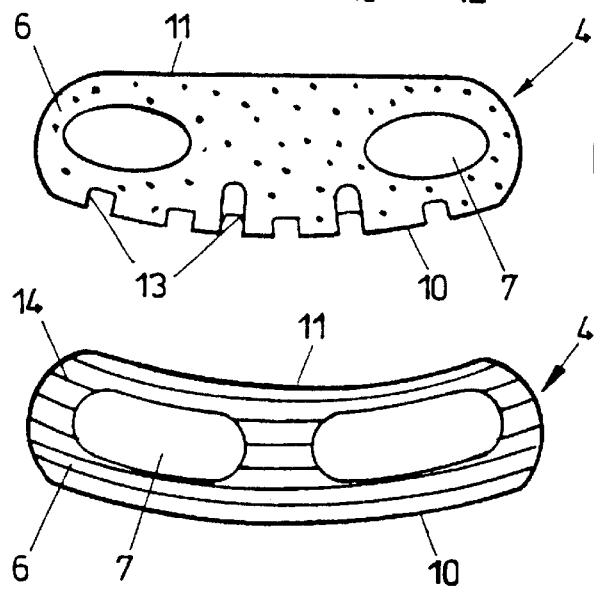
FIG. 2b
FIG. 2c

FIG. 3
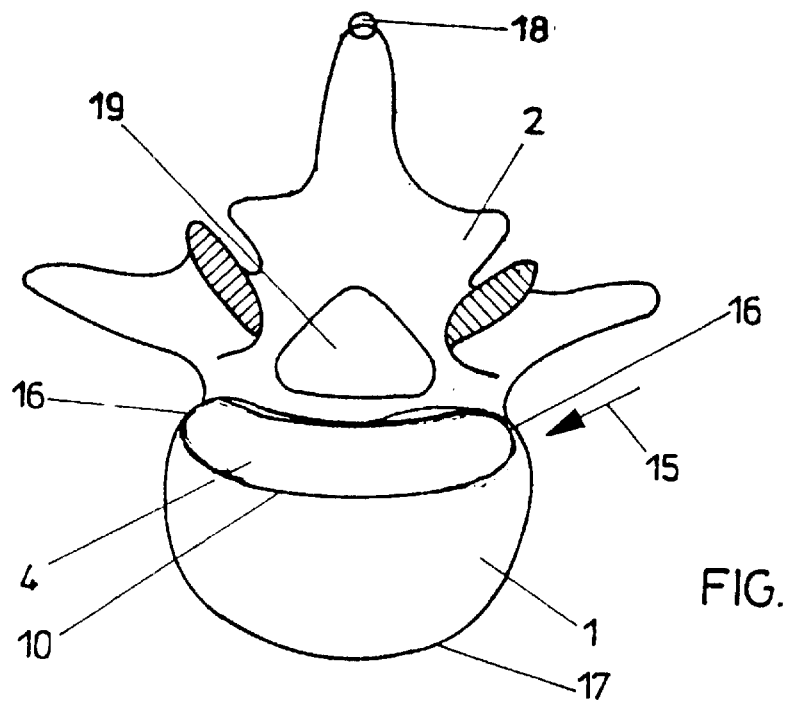
FIG. 3a
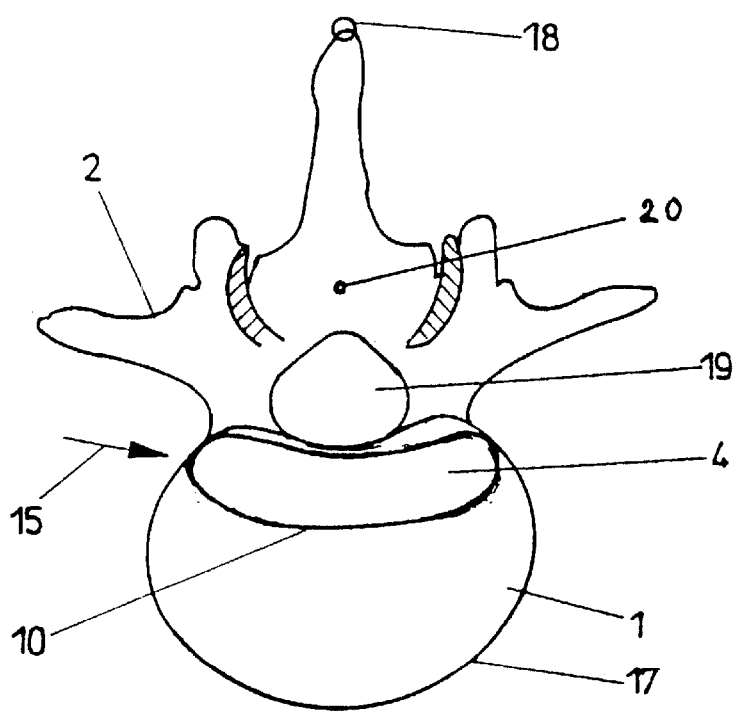
FIG. 3b

FIG. 3
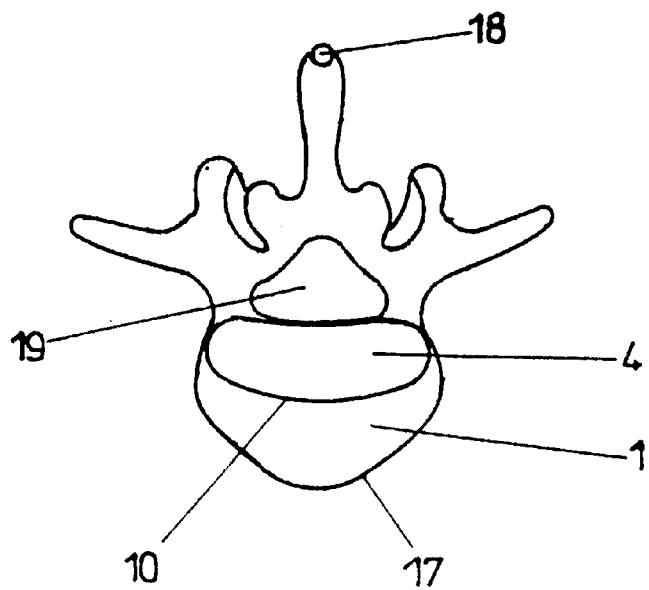
FIG. 3c
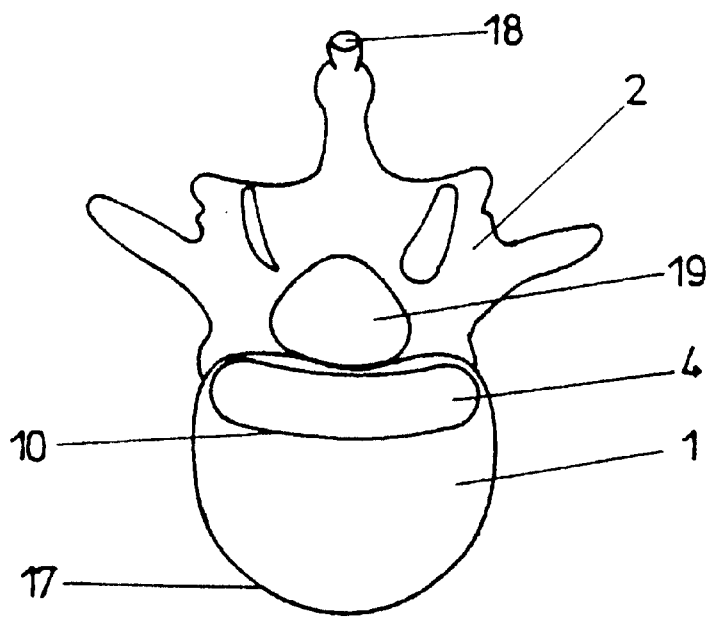
FIG. 3d

IMPLANT FOR INSERTION BETWEEN SPINAL COLUMN VERTEBRAE This application is a continuation of international application number PCT/AT99/00015 filed on Jan. 22, 1999.

BACKGROUND OF THE INVENTION

The present invention relates to an implant for insertion between the vertebrae of the spinal column, whereby the cover surfaces of the substantially rectangular- or trapezoidal-section implant facing the adjacent vertebrae are porous and/or are provided with a profiled structure.

Implants of this type are used to form supports for vertebral fusions, whereby, after at least a partial removal of an intervertebral disc and preparation of the roof plates of the vertebrae, the implant that is to be inserted between adjacent vertebrae is introduced into the intervertebral interstice, and it is ensured that the intervertebral space is kept clear. By forming the cover surfaces facing the adjacent vertebrae with a porous surface or providing them with a profiled structure, the arrangement will become firmly anchored after the implant has been inserted due to the growth of the bones of the adjacent vertebrae onto the cover surfaces of the implant. In addition, or, as an alternative, at least one break-through or recess in the cover surface of such an implant may be filled with bone mass before being inserted so that the bone mass accommodated in the implant will be urged to knit with the material of the immediately adjacent vertebrae after the implant has been inserted. Moreover, a support system extending over a plurality of vertebrae may be provided externally of the spinal column near the implant for lending additional support, said system being attachable to the individual vertebrae.

Implants of the type mentioned hereinabove can be derived from U.S. Pat. No. 4,834,757, U.S. Pat. No. 5,192,327 or WO 90/00037 for example. In the construction according to U.S. Pat. No. 4,834,757, implants of substantially rectangular cross-section are made use of, whereby two implants are inserted posteriorly between respective pairs of adjacent vertebrae in each of the two side regions of the vertebrae. The disadvantage of this known construction is that, in addition to an at least partial removal of the rear bony and ligamentary elements which is necessary to allow insertion of the implant, it is imperative that two separate implants be used, this thereby not only resulting in increased expenditure for the operation but also requiring that they be mutually correctly positioned, something which it is not easy to achieve.

In the construction according to WO 97/00037, an implant is inserted whose outer dimensions substantially correspond to the total dimensions of two adjacent vertebrae. A particular disadvantage with implants of this type is that in practice they can only be inserted anteriorly, whereby however, in addition to the complicated access via the abdominal cavity with consequent possible injury to the major abdominal vessels and the nerve plexus, the frontal longitudinal ligament has to be cut-through so that the natural supporting function exercised by this longitudinal ligament is no longer available after the implant has been inserted. Moreover, a further operation then has to be effected posteriorly for the insertion of an additional support structure that thereby becomes necessary.

In addition to these embodiments of implants for insertion between vertebrae of the type described above, other implants having substantially cylindrical contours are known, for which reference may be made to EP-A 0 369 603 or DE-C 36 37 314 for example. Such types of cylindrical or tube-shaped implants may be additionally provided with a thread-like outer contour in order to enable them to be screwed between the vertebrae by means of a self-threading action. The particular disadvantage of tube-shaped implants of this type, whereby two implants must again be used between each two adjacent vertebrae in normal circumstances, is that the implants will not have a defined substantially flat support area on the vertebrae thus giving rise to the fear that difficulties will possibly be encountered in regard to the growth of the incorporated bony material. Another disadvantage is that injury to soft bony parts with consequential breakage or subsidence of the bone may be induced by the threading or screwing actions.

Based upon the above-mentioned state of the art, the aim of the present invention is then to provide an implant for insertion between the vertebrae of the spinal column, whereby an adequate and reliable supporting function can be achieved using merely one implant between two vertebrae and wherein the implant in accordance with the invention should be insertable posteriorly, especially laterally, so as, firstly, to simplify the operation and enable the implant to be inserted together with an additional support system if required and secondly, to avoid the necessity of damaging or destroying naturally provided support elements such as the frontal longitudinal ligament for example and/or to avoid having to remove additional ligamentary and bony material, especially in the region of the vertebral or spinous process, in order to allow the implant to be inserted.

SUMMARY OF THE INVENTION

Based upon an implant of the type mentioned hereinabove, the above object is achieved by the implant in accordance with invention, in essence, in that the breadth of the implant is such that it covers at most the rearward half of the vertebra facing the spinous process, and preferably at most the rearward third thereof, and the length of the implant is essentially such that it overlaps the rearward region of the vertebra, and in that the boundary face of the implant facing the interior of the vertebra and extending towards the adjacent vertebrae is curved convexly. Due to the fact that the implant in accordance with the invention basically covers only the rearward portion of the adjacent vertebrae when it is in the installed state, the requisite reach can be found with an appropriately miniature implant, whereby the largest forces and loads are effective in the rear portion of the vertebrae facing the vertebral or spinous process and can thus be reliably accommodated in a corresponding manner by the implant in accordance with the invention, and also the bone strength is at its greatest in said rear portion. In addition to a miniature, one-piece construction of the implant as proposed in accordance with the invention, it is also possible to introduce the implant laterally between and passing-by the protruding nerve roots and the spinal cord into the intervertebral space from behind, especially by virtue of the further matter envisaged in accordance with the invention, namely, the convexly curved boundary face facing the interior of the vertebra when in the installed state, so that, in the case of a posterior operational technique of this type, not only will the frontal longitudinal ligament remain completely undamaged, but one can also dispense with the additional removal of ligamentary and bony material such as was required for implants in accordance with the state of the art. By virtue of the curved boundary face, not only is it possible to ensure a simple sideways introduction of the implant, but exact positioning of the implant can also be achieved so as to cater for the portion of the vertebrae facing the spinous process being covered in the inserted state and thereby providing proper support.

In order to simplify still further the lateral introduction of the implant, provision is preferably made for the boundary face of the implant facing the spinous process to be curved concavely so that overall, when seen from a top view, there will be provided an essentially bow or crescent shaped implant which is correspondingly easily and reliably introducible from the side into the intervertebral space from the rear with the very smallest amount of space being required.

Moreover, for the purposes of adequately supporting adjacent vertebrae by covering an appropriate portion thereof, it is proposed that the radius of curvature of the boundary face of the implant facing the interior of the vertebra amount to 30 to 90%, and especially to 40 to 80%, of the spacing between the frontal edge of the vertebra and the peak of the spinous process, as corresponds to a further preferred embodiment of the implant in accordance with the invention.

For the purposes of matching the outer contours of the vertebrae in the portion facing the spinous process and also for maintaining sufficient spacing between the implant and the vertebral canal, it is proposed in another preferred embodiment that the radius of curvature of the boundary face of the implant facing the spinous process amount to 10 to 80%, and especially to 20 to 60%, of the spacing between the frontal edge of the vertebra and the peak of the spinous process. Thus, in the case of the implant in accordance with the invention, adaptation to vertebrae of various sizes or to vertebrae located at differing parts of the spinal column can be obtained by appropriate selection of the radius of curvature of the boundary faces.

As was mentioned hereinabove, the implant may be filled with bone mass prior to insertion in order to enable it to knit with the surrounding bone material of the vertebra so as to achieve the desired level of support in the subsequent part of the process. However, in order to prevent a build up of bone mass from the implant covering the rearward section of the vertebrae towards the spinous process, and especially towards the vertebral canal, additional provision is preferably made for the boundary face facing the spinous process to be substantially free of break-throughs or recesses. This boundary face thus makes a defined surface of the implant available from which there will be no fear of an issue of bone mass from the interior of the implant.

Since, when in its installed state, the implant in accordance with the invention merely covers a portion of the surface of the vertebrae, the intervertebral space located outside this portion may, in accordance with the invention, also be filled with bone material before the insertion of the implant and after the removal of the intervertebral disc thereby producing a substantially fully filled intervertebral space after the implant has been inserted. In this context and for the purposes of connecting the bone mass outside and within the implant in the intervertebral space, it is preferably proposed that the boundary face facing the interior of the vertebra comprise at least one recess or depression or break-through. Due to this at least one recess, depression or break-through in the boundary face facing the interior of the vertebrae, knitting or growth of the bone mass in the intervertebral space can thus be achieved, whereby this knitting of the implant with the surrounding bone material can easily be checked and confirmed by means of an X-ray examination for example. Furthermore, due to the formation of a depression or recess, a central, thinner region of the implant can be obtained so that it can be introduced more easily into the intervertebral space when the spatial conditions are very tight thereby encouraging the process of knitting with the surrounding bone material. Furthermore, an implant having a recess or depression of this type can be fed past the nerve root without displacement thereof during the insertion process. Moreover, a bone graft inserted in the intervertebral space not covered by the implant and having a bow-shaped or convex surface or outer contour can be placed in contact with such a depression or recess over a larger peripheral area thereby encouraging the subsequent knitting process.

In order to avoid injuring the region of the spinal column surrounding the implant and in order to ensure a substantially form-fitting seal between the implant and the outer contours of the vertebrae after the installation of the implant, provision is made for the outer faces of the implant facing the laminae to be rounded, and, in particular, to substantially follow the outer contour of the vertebra in the vicinity of the laminae, as corresponds to another preferred embodiment of the implant in accordance with the invention.

For the purposes of easily gripping the implant by appropriate instruments during the insertion process or when removing or replacing it, further provision is preferably made for a respective opening to be provided in the outer faces, said opening being provided, in particular, with a thread and being closable if required.

In addition to the provision of openings, especially those with a thread, for gripping or positioning the implant in accordance with the invention, provision is made in accordance with another preferred embodiment for at least one opening or boring extending, in particular, at an angle to the longitudinal axis of the implant to be provided, said opening commencing from at least one outer face and/or from the boundary face opposite the convexly curved boundary face and ending in the convexly curved boundary face facing the interior of the vertebra. By virtue of such an opening or boring extending, in particular, at an angle to the longitudinal axis of the implant and ending in the convexly curved boundary face facing the interior of the vertebra, it is possible, after the insertion of the implant, to subsequently compress the bone material located in the region within the vertebra by using an appropriate rod or tube-shaped tool or instrument, or, to introduce additional bone material through an opening of this type so as to ensure a corresponding firm retention of the implant and to assist in subsequent knitting of the implant to the surrounding bone material. Provision may hereby be made either for small pieces of bone material to be arranged in the region of the intervertebral space not covered by the implant, or, for a bone graft from the iliac crest for example to be inserted so that, by virtue of the opening extending, in particular, at an angle to the longitudinal axis of the implant, it becomes possible for this bone graft to be subsequently appropriately positioned or for any possibly remaining free space to be subsequently filled with additional bone material or for proper compression thereof to be effected. Hereby, provision may further be made for the opening ending in the region of the outer surfaces and having a thread for co-operating with an instrument to be extended directly through the opening ending in the region of the convexly curved boundary face so that such a continuous opening or such a canal can be utilised firstly for inserting the implant by using an appropriate tool, and thereafter for stopping-up or filling the intervertebral space using an instrument or tool having a diameter less than that of the threaded portion.

In order to be able to traverse a further region of the intervertebral space through such an opening extending, in particular, at an angle to the longitudinal axis of the implant, provision is made in accordance with a further preferred embodiment for the opening or boring to be formed such that it widens out conically towards the convexly curved boundary face. A tool of appropriately small dimensions can thus be introduced into the intervertebral space at differing angles of inclination by virtue of such a conically widening opening.

In order to enable adaptation to the anatomically ordained curvature of the spinal column and to retain the biomechanical functioning of the spinal column, provision is made in another preferred arrangement for the cover surfaces of the implant resting on the adjacent vertebrae to include an acute angle therebetween, whereby the particularly preferred proposal is made that the angle included between the cover surfaces amount to at most 25°, and especially to at most 15°.

For the purposes of supporting the connection of the implant to the surrounding material of the vertebrae and to ensure firm anchorage of the implant, the boundary faces of the implant extending towards the adjacent vertebrae are made porous and/or are provided with a profiled structure, in particular, by means of a plurality of elevations and depressions, such as corresponds to another preferred embodiment of the invention. In accordance with an especially preferred embodiment, provision may be made in this context for the porous surface to be formed by sandblasting or vacuum deposition.

In addition to the hollow spaces or breakethroughs required for the bone mass filling process, it is necessary to provide an adequate support function and a firm anchorage for the implant which is comparatively long since it covers substantially the whole outer spacing of the laminae, so that, in accordance with the invention, provision is preferably also made for the implant to be substantially hollow at least in the direction of the adjacent vertebrae between the boundary faces facing the interior of the vertebra and the spinous process, whereby, in addition to the outer surfaces connecting the boundary faces, there is provided at least one web-like connection extending towards the outer surfaces between the boundary faces. The strength of the implant is corresponding increased by virtue of at least one such web-like connection, whereby however, an adequately large amount of free space still remains in the implant for filling it with bone mass or to allow subsequent growth.

Thus, the implant in accordance with the invention can be made to be substantially solid or holohedral and be substantially free of continuous break-throughs or recesses extending towards the adjacent vertebrae, thereby resulting overall in the provision of a large surface area for application to the adjacent vertebrae and hence better support therefor and an overall increase in the strength of the implant in accordance with the invention. In the case of a construction of this type, rooting or growth of the surrounding bone material, essentially on the cover surfaces and the boundary faces extending towards the adjacent vertebrae, is thereby obtained with consequentially secure anchorage of the implant in the intervertebral space. The profiled structures provided in the region of the cover surfaces and the boundary faces extending towards the adjacent vertebrae and/or an at least partially porous surface on these boundary faces serve to assist such rooting or outward growth. Due to the provision of at least one break-through extending towards the adjacent vertebrae so that the interior of the implant in accordance with the invention is at least partially hollow, the bone material disposed in the hollow cavity following the insertion of bone material into this hollow region can knit with the adjacent bone surfaces, or, bone material can grow directly through hollow cavities of this type.

BRIEF DESCRIPTION OF THE DRAWINGS

The invention will be explained in more detail hereinafter with the aid of the embodiments of the implant in accordance with the invention schematically illustrated in the accompanying drawing. Therein FIG. 1 shows a schematic, partial side view of two adjacent vertebrae between which an implant in accordance with the invention has been inserted;

DETAILED DESCRIPTION OF THE INVENTION

Figure 2D:
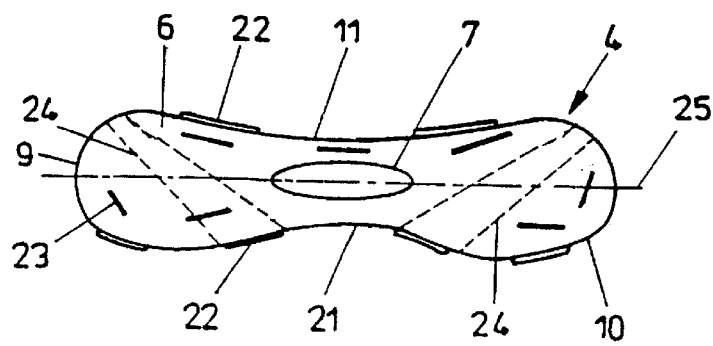
FIG. 2 shows schematic top views of differing embodiments of an implant in accordance with the invention.

In FIG. 1, two schematically illustrated adjacent vertebrae are referenced 1 and the respective vertebral processes of the vertebrae 1 are referenced 2.

Following the removal of an intervertebral disc in a frontal region, bone mass is provided in the intervertebral space 3 whilst an implant 4, which is illustrated in more detail in FIGS. 2 and 3, is inserted in the region facing the spinous or vertebral process 2. The implant 4 has a schematically indicated opening 5 in the outwardly facing outer surface thereof, said opening serving for the application or fixing of an instrument during the process of inserting the implant 4 and being closable if necessary when the implant is in its installed state. Furthermore, the implant 4 comprises cover surfaces 6 which abut the vertebrae 1 and include an acute angle therebetween amounting to e.g. 10d to 15a in the embodiment shown in FIG. 1. By virtue of this angle between the cover surfaces 6, one can adapt to the curvature of the spinal column and to the bio-mechanical properties of the spinal column whereby, in the case of the differing vertebrae 1 illustrated in FIG. 3, it is possible to take appropriate account of the various curvatures of the spinal column in different parts thereof by additionally selecting the angle between the cover surfaces 6 as well as by selecting implants 4 of different sizes.

Furthermore, it is apparent from FIG. 1, and in greater detail from FIG. 3, that the implant 4 is arranged in only the portion of the vertebra 1 facing the vertebral processes 2 when it is in its inserted state, whereby the greatest forces and loads are effective in this rearward portion and consequently it is possible for the implant 4 to provide effective support for the vertebrae 1 and to accommodate the loads.

Differing embodiments of the implant 4 are illustrated in greater detail in the form of top views in FIG. 2. In the case of the construction according to FIG. 2a, it is apparent that the implant 4 comprises three substantially vertically extending continuous recesses or break-throughs 7 which are filled with bone mass prior to installation of the implant 4 so that it can knit with the directly abutting vertebrae 1 after the implant 4 has been inserted between the vertebrae 1. The break-throughs 7 are bounded longitudinally of the implant 4 by web-like connections 8 and the outer surfaces 9 of the implant 4 so as to obtain a suitably resistive, very sturdy construction. The boundary faces of the implant 4 towards the interior of the vertebrae 1 and towards the vertebral processes 2 are referenced 10 and 11 respectively.

In FIG. 2a, the openings provided in the outer surfaces 9 for gripping the implant 4 by means of not particularly illustrated instruments are again referenced 5 and furthermore, schematically indicated openings or breakthroughs 12 can be perceived in the convexly curved boundary faces 10 of the implant facing the interior of the vertebrae 1. In addition to a connection to the surrounding bone mass through the break-throughs 7, a connection between the bone material introduced into the interior of the breakthroughs 7 and the surrounding bone material 3 of the intervertebral space can also be effected through the openings 12. By contrast, the boundary face 11 of the implant 4 facing the spinous process does not incorporate openings or breakthroughs so as to avoid bone material issuing out at such points or to prevent any possible intrusion thereof into the vicinity of the adjoining vertebral canal, as is clearly apparent from FIG. 3.

It is also perceptible from FIG. 2a that the implant 4 as viewed from above has a substantially bowed or crescent-like outer contour which enables it to be easily and safely introduced laterally into the intervertebral space from behind, as is also clearly apparent from FIG. 3.

In the construction according to FIG. 2b, substantially vertical break-throughs 7 are again provided for accommodating bone material. Instead of or, if so required, in addition to the recesses 12 in the curved boundary face 10, set-back or undercut portions or breakthroughs 13 are provided in this construction, these breakthroughs being substantially perpendicular to or extending towards the adjacent vertebrae, thereby likewise enabling secure anchorage of the implant 4 due to intrusion of bone material into these cut-out areas or depressions 13. For the purposes of assisting the anchorage process, provision may also be made in this construction for at least the boundary face 10 and the cover surfaces 6 of the implant 4 to be suitably roughened or made porous so as to facilitate connection with the surrounding bone material. In the construction according to FIG. 2b, it is apparent that, apart from the again convexly curved boundary face 10 which assists the process of laterally introducing the implant 4, the boundary face 11 is made substantially straight or even, thereby possibly simplifying the manufacture of the implant 4.

In the construction according to FIG. 2c, profiled structures 14 in the form of elevations and depressions are provided on the cover surfaces 6, these extending substantially in correspondence with the curvature of the boundary faces 10 and 11 and enabling additional anchorage to be provided for the implant 4.

In the illustration according to FIG. 2d, which is a modification of the embodiment according to FIG. 2b, only one depression or recess 21 is provided on the convexly curved boundary face 10 thus resulting in the central section of the implant 4 being of lesser thickness than the wall regions whereby an improvement in the process of introducing the implant 4 in the vicinity of the nerve root and thereby a lesser risk of injury can be achieved, as will become still more clearly apparent from a consideration of the succeeding FIG. 3. Moreover, provision is made for profiled structures or elevations to be formed on the boundary faces 10 and 11, these being raised thereabove as indicated schematically by the references 22 and enabling the knitting process with the surrounding bone material to be effected more easily. Similar profiled structures or elevations or complementary depressions are also provided on the cover surfaces 6 as indicated by the references 23 whereby, as a modification of the embodiment according to FIG. 2c, these profiled structures are of shorter extent compared to the total extension of the cover surface 6 whereas, in the construction according to FIG. 2c, the profiled structures extend substantially continuously over the whole cover surface 6. Instead of profiled structures or elevations 22, 23 of this type, an appropriately rough or porous surface may be provided on the cover surfaces or the boundary faces 9, 10 and 11 in like manner to that of the embodiment according to FIG. 2b, this type of surface being produced by sandblasting or vacuum deposition for example.

In the construction according to FIG. 2d, there are provided openings or borings 24, which commence from the outermost boundary faces 9 and ends in the convexly curved boundary face 10, these openings being indicated by the dashed lines and extending at substantially half the height of the implant 4. As is apparent from the illustration according to FIG. 2d, these openings or borings 24 widen conically towards the boundary face 10. The inlet openings provided in the outer surfaces 9 may, for example, be provided with a thread in a manner directly similar to that of the break-through 5 so as to enable it to be gripped by an instrument when introducing the implant 4. Once the insertion process has been accomplished, then, by using an instrument or packing tool of lesser diameter, this may be introduced through the continuous opening 24 into the region in front of the convex surface 10 or into the region of the depression 21 so as to enable bone mass, which is, for example, already present in the intervertebral space, to be compacted at these points. If necessary, additional bone material may be inserted through these openings 24 into the region located in front of the convex boundary surface 10 where it is then compacted. Hereby, it is also apparent from FIG. 2d that the opening or boring 24 extends at an angle to the longitudinal axis of the implant 4 which is indicated schematically by the reference 25.

Figure 2E:
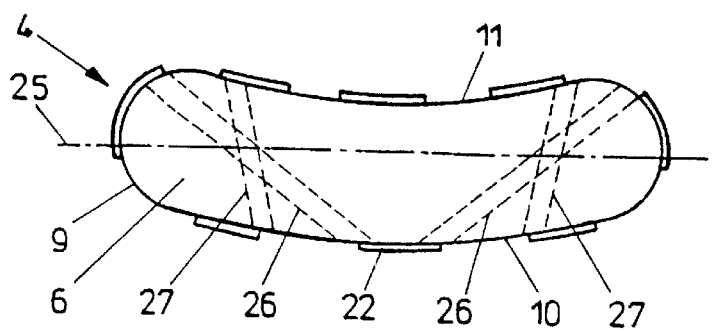

In the case of the modified embodiment according to FIG. 2e, profiled structures or elevations again referenced by 22 are indicated on the outer boundary faces 9 as well as on the concave and convex boundary faces 10 and 11, whereby similar profiled structures may also be provided on the respective cover surfaces 6. Whereas, in the construction according to FIG. 2d, the continuous boring or opening 24 widens out conically so as to enable a large region to be swept by a packing tool, in the embodiment according to FIG. 2e, there are provided mutually crossing borings 26 and 27 which again extend at an angle to the longitudinal axis 25 of the implant 4 and again enable bone mass located in front of the convex boundary surface 10 to be consolidated by using an appropriate packing tool. The end of the boring 26 ending in the region of the outer surface 9 may again cooper ate with a tool for inserting the implant 4. It is also apparent from FIG. 2e that, apart from a porous surface or corresponding profile d structures on the cover surfaces 6, no break-throughs extending, especially completely, through the implant 4 are provided so that a correspondingly massively constructed implant 4 of great rigidity can thereby be achieved.

Differing vertebrae having implants 4, whose size is matched to the respective vertebra, arranged thereon are illustrated schematically in FIG. 3. By virtue of their boundary face 10 which is curved convexly at least towards the interior of the vertebra 1, the implants 4 can be introduced sideways from the rear in the sense of the arrow 15 without it being necessary to remove ligamentary and bony material in the vicinity of the vertebral process 2. Furthermore, it is apparent from FIG. 3 that the breadth of the implants 4 is such that the respective implants 4 only cover the rearward region facing the vertebral processes 2, in particular, up to at most half of the vertebra 1 as indicated in FIG. 3c, or approximately one third of the surface area of the vertebra 1, whereas the length of the implants 4 corresponds substantially to the total extension of the vertebra 1 in this region, and, in particular, to the length of the outer spacing of the laminae 16.

Moreover, the radius of curvature of the boundary face 10 falls within the range from 30 to 90%, and especially 40 to 80%, of the spacing between the frontal edge 17 of the vertebra 1 and the peak 18 of the spinous process 2, whereby the centre point of the circle defining the boundary face 10 is chosen as the apex 18 of the spinous process 2 in the construction according to FIGS. 3a, 3c and 3d. By contrast, in the construction according to FIG. 3b, the centre point of the circle is chosen to be at the base of the spinous process 2 where it is referenced 20, whereby the overall task of introducing the implant 4 in correspondence with the arrow 15 is simplified still further due to the greater curvature thereof in the embodiment illustrated in FIG. 3.

Furthermore, in the case of a bow-shaped construction of the implant 4 such as is illustrated in detail in FIGS. 2a and 2c to 2e for example, the radius of curvature of the boundary face 11 of the implant 4 facing the spinous process 2 may amount to between 10 and 80%, and especially 20 to 60%, of the spacing between the frontal edge 17 of the vertebra 1 and the peak 18 of the spinous process 2, whereby the respective positions 18 and 20 are again chosen as the central points of revolution.

In each case, the vertebral canal, which must be especially protected, is referenced 19 in FIG. 3.

Figure 3E:
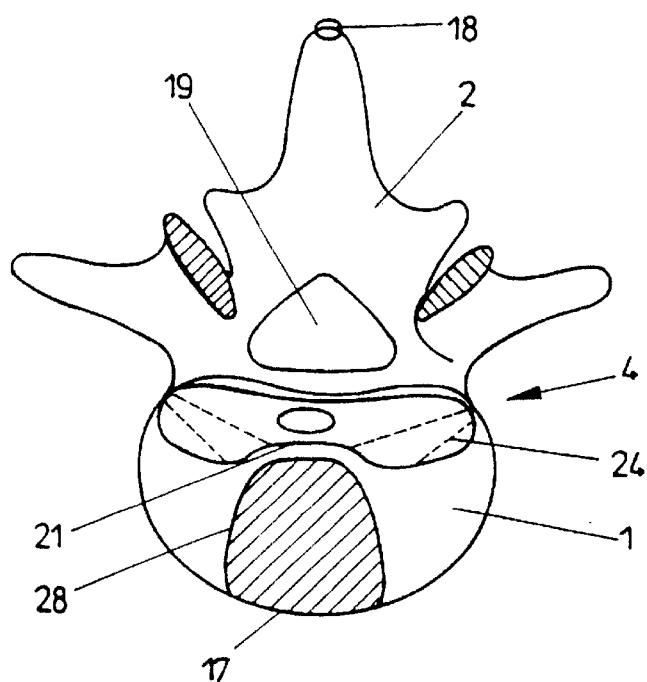
FIG. 3 shows schematic top views of differing vertebrae having implants in accordance with the invention arranged thereon for illustrating the positioning of the implants in their inserted state.

In the illustration of FIG. 3e, it is indicated that a schematically illustrated bone graft, which is referenced 28 and may be taken from the iliac crest for example, has been inserted in the intervertebral space that is not covered by the implant 4. After the introduction of the implant 4 between adjacent vertebrae 1 in the case of the schematically indicated embodiment of an implant 4 which corresponds to the implant according to FIG. 2d for example, subsequent filling of the intervertebral space or compacting of material in the region of the separately inserted bone graft 28 can be effected through the openings which are again indicated by the reference 24. Furthermore, it is indicated in FIG. 3e that, due to the provision of a depression 21 of this type, not only is the task of introducing the implant 4 simplified whilst reducing the risk of injury in the vicinity of the nerve root, but also a correspondingly larger bone graft 28 can be inserted thereby enabling a correspondingly secure anchorage of the implant 4 and connection to the surrounding material to be obtained by virtue of the enlargement of the surface provided by the depression 21 and the additional provision of appropriately profiled structures which are not illustrated in FIG. 3e for the sake of simplicity.

Naturally, instead of the respective implants 4 schematically indicated in FIG. 3, any of the implants shown in the other Figures may be used so as to enable the wanted effects to be achieved or to adapt to the relevant requirements. Furthermore, individual features of the differing embodiments of implants 4 illustrated, in particular, in FIGS. 2a to 2e, may of course be appropriately combined to form modifications of the illustrated constructions so as to achieve the wanted properties for an implant 4.

What is claimed is:

1. An implant for insertion between the vertebrae of a spinal column, wherein:

surfaces of a substantially rectangular or trapezoidal-section implant adapted to face adjacent vertebrae are porous and/or are provided with a profiled structure, a breadth of the implant is adapted to cover at most a rearward half of the vertebra facing the spinous process, a length of the implant is adapted to essentially overlap the rearward region of the vertebra, a first boundary face of the implant adapted to face the interior of the vertebra and extend towards the adjacent vertebrae is curved convexly over at least a portion of a wall of said first boundary face, a second boundary face of the implant adapted to face the spinous process is curved concavely, said second boundary face being free of break-throughs, the first boundary face comprises at least one depression which extends into, but not through, said wall of said first boundary face, and two borings extending through the implant, wherein each boring runs from respective outer faces of said implant into said depression in a central portion of the implant.

2. An implant in accordance with claim 1, wherein outer faces of the implant adapted to face laminae are rounded.

3. An implant in accordance with claim 1, wherein a respective opening is provided in outer faces of the implant adapted to face the laminae.

4. An implant in accordance with claim 3, wherein the opening is closable.

5. An implant in accordance with claim 1, wherein at least one opening is provided, said opening commencing from at least one outer face and ending in the convexly curved first boundary face.

6. An implant in accordance with claim 5, wherein the opening extends at an angle to a longitudinal axis of the or, implant.

7. An implant in accordance with claim 5, wherein the opening widens out conically towards the convexly curved first boundary face.

8. An implant in accordance with claim 1, wherein cover surfaces of the implant adapted to rest on the adjacent vertebrae include an acute angle therebetween.

9. An implant in accordance with claim 8, wherein the angle included between the cover surfaces is no greater than about 15°.

10. An implant in accordance with claim 1, wherein the profiled structure is formed by a plurality of elevations and depressions.

11. An implant in accordance with claim 1, wherein the porous surface is formed by sandblasting or vacuum deposition.

12. An implant in accordance with claim 1, wherein the depression is adapted to extend towards the adjacent vertebrae.

13. An implant in accordance with claim 12, wherein the depression is located in a central portion of the implant.

14. An implant in accordance with claim 14, wherein the thickness of the implant in the central portion thereof is less than that of outer sections adjoined thereto due to the depression.

15. An implant in accordance with claim 1, wherein the depression is located in a central portion of the implant.

16. An implant in accordance with claim 1, wherein the thickness of the implant in a central section thereof is less than that of the outer sections adjoined thereto due to the depression.

17. An implant in accordance with claim 1, wherein the implant is constructed symmetrically relative to a center plane perpendicular to the longitudinal axis of the implant.

18. An implant in accordance with claim 1, wherein the profiled structure is formed by a plurality of ribs.

19. An implant in accordance with claim 1, wherein the depression extends over the entire height of the implant.

20. An implant in accordance with claim 1, wherein the depression is formed by a concave central portion of the first boundary face, which central portion has an arc-shaped contour.

21. An implant in accordance with claim 20, wherein side portions of the first boundary face, which side portions adjoin the central portion, run in an arc-shaped manner continuously into said central portion.

22. An implant in accordance with claim 21, wherein the side portions extend substantially parallel to side portions of the second boundary face.

* * * * *